US005989898A

United States Patent [19]

Jin et al.

[11] Patent Number: 5,989,898

[45] Date of Patent: Nov. 23, 1999

[54] METHOD FOR STORING FUNGAL CONIDIA

[75] Inventors: Xixuan Jin; Kathryn E. Grigas; Carol Ann Johnson, all of Worcester; Paul Perry, Acton; David W. Miller, Amherst, all of Mass.

[73] Assignee: EcoScience Corporation, East Brunswick, N.J.

[21] Appl. No.: 08/068,997

[22] Filed: May 27, 1993

Related U.S. Application Data

[63] Continuation-in-part of application No. 07/889,594, May 27, 1992, abandoned.

[51] Int. Cl.[6] ................................ C12N 1/04; C12N 1/14

[52] U.S. Cl. ........................ 435/260; 435/254.1; 424/93.5

[58] Field of Search ................................ 435/254.1, 260; 424/93 Q, 93.5

[56] References Cited

U.S. PATENT DOCUMENTS

| | | | |
|---|---|---|---|
| 3,338,794 | 8/1967 | Bladel . | |
| 3,360,440 | 12/1967 | Haab et al. . | |
| 3,865,695 | 2/1975 | Massier . | |
| 4,063,383 | 12/1977 | Green . | |
| 4,097,261 | 6/1978 | Conway et al. . | |
| 4,235,964 | 11/1980 | Bochner . | |
| 4,311,477 | 1/1982 | Kitamura et al. . | |
| 4,390,360 | 6/1983 | Walker . | |
| 4,530,834 | 7/1985 | McCabe et al. . | |
| 4,718,935 | 1/1988 | Walker et al. . | |
| 4,724,147 | 2/1988 | Marois et al. . | |
| 4,751,082 | 6/1988 | Schaerffenberg et al. . | |
| 4,765,275 | 8/1988 | Yukawa et al. . | |
| 4,878,312 | 11/1989 | Shimizu . | |
| 4,886,664 | 12/1989 | Jung et al. . | |
| 4,908,315 | 3/1990 | Kertz . | |
| 4,921,703 | 5/1990 | Higuchi et al. . | |
| 4,925,663 | 5/1990 | Stimac . | |
| 4,978,505 | 12/1990 | Kertz . | |
| 5,042,427 | 8/1991 | Bedding . | |
| 5,057,315 | 10/1991 | Gunner et al. ........................ | 424/93 Q |
| 5,057,316 | 10/1991 | Gunner et al. . | |
| 5,074,902 | 12/1991 | Connick et al. . | |
| 5,088,231 | 2/1992 | Kertz . | |
| 5,141,744 | 8/1992 | Chang et al. . | |
| 5,238,681 | 8/1993 | Chang et al. . | |

FOREIGN PATENT DOCUMENTS

| | | |
|---|---|---|
| 81386/87 | 11/1987 | Australia . |
| 0226394 | 6/1987 | European Pat. Off. . |
| 92100010 | 1/1992 | European Pat. Off. . |
| WO 89/12385 | 12/1989 | WIPO . |
| WO 90/15526 | 12/1990 | WIPO . |

OTHER PUBLICATIONS

Walstad, J.D., "Effects of Environmental Conditions on Two Species of Muscardine Fungi (*Beauveria bassiana* and *Metarhizium anisopliae*)", *J. of Invertebrate Pathology*, vol. 16, 221–226 (1970).

Beker & Rapoport, Conservation of Yeast by Dehydration, In Advances in Biochemical Engineering/Biotechnology, vol. 35 of Biotechnology Methods, ed. A. Fiechper, Springer Verlag, pp. 127–171 (1987).

Crowe & Crowe, Stabilization of Membranes in Anhydrobiotic Organisms In Membranes, Metabolism and Dry Organisms, A.C. Leopold, Comstock Publishing Co., Ithica, NY, pp. 188–209 (1986).

Dillon, Roderick James and Anthony Keith Charnley, "A technique for accelerating and synchronising germination of conidia of the entomopathogenic fungus *Metarhizium anisopiiae," Arch. Microbiol.* 142:204–206 (1985).

Zweig, Gunter, "Environmental Aspects of Controlled Release Pesticide Formulations," *Controlled Release Pesticides* Amer. Chem. Soc., Washington, D.C. 37–53 (1977).

Smith, In "Maintenance of Microorganisms", Kirsop et al ed. 1988, pp. 87–91.

ATCl Catalogue of Filamentous Fungi, 1991, pp. xv–xvi, 74–75, 235–236.

Roberts et al., Entomol. Sci. Am., vol. 10, pp. 19–76 (1977).

Daoust et al., J. of Invert. Path., 41, pp.143–150 (1983).

Daoust et al., J. of Invert. Path., 41, pp.151–160 (1983).

Daoust et al. J of Invert. Path., 41, pp. 161–170 (1983).

Reinecke et al. Brighton Crop Protection Conf.—Pests & Diseases, pp. 49–54 (1990).

Ferron, Ann. Rev. Entamol., 23, pp. 409–442 (1978).

*Primary Examiner*—Irene Marx
*Attorney, Agent, or Firm*—Arnall Golden & Gregory, LLP

[57] ABSTRACT

Methods for packaging Metarhizium fungal cultures or conidia are described. In one embodiment, the fungal culture is provided within an insect infection chamber that attracts insects, then infects them with a lethal dosage of fungus, where the packaging maintains high humidity within the chamber, allows free exchange of gases, and is impermeable to microbes, including fungal spores, viruses, and bacteria. In a second embodiment, the fungal conidia are packaged under conditions which maintain high viability even after long-term storage at both 25° C. and 37° C., i.e., low relative humidity and oxygen. The conidia can then be reactivated for the use in the control of insects such as cockroaches, flies, ants, soft-bodied insects, turf pests, and caterpillars.

8 Claims, 7 Drawing Sheets

METHOD FOR STORING FUNGAL CONIDIA

This is a continuation-in-part of U.S. Ser. No. 07/889,594, filed May 27, 1992, now abandoned, entitled "Storage Conditions for Infective Chamber for Insects," by David W. Miller, Paul Perry, and Carol Ann Johnson.

There are many varieties of insects that cause major economic losses in agriculture and spread diseases among human and other animal populations. Currently, application of different chemical pesticides is the approache employed to control these insects. Unfortunately, pesticides are expensive and generally hazardous to the environment, particularly if effective for more than a very short term. Further, there is a tendency for pesticide-resistant strains of insects to develop, which requires the use of large quantities of pesticides, and re-treatment with different chemicals. The use of chemical insecticides also results in the destruction of non-target insects.

BACKGROUND OF THE INVENTION

The present invention relates to an improved means and methods of storage and reactivation of entomopathogenic fungal cultures and conidia, especially of the genera Metarhizium.

Insect pathogens are an alternative to the common use of highly toxic chemical insecticides for the control of insect pests. Bacteria such as *Bacillus thurigenesis* are used with some success as a spray on plants susceptible to infestation with insects such as the gypsy moth. Fungi are another promising group of insect pathogens suitable for use as biological agents for the control of insects. The most common mode of growth and reproduction for fungi is vegetative or asexual reproduction which involves sporulation followed by germination of the spores. Asexual spores, including conidia, form at the tips and the sides of sporogenous cells on the hyphae, the branching filamentous structures of multicellular mycelium. In the proper environment, the conidia germinate, become enlarged,and produce germ tubes. The germ tubes develop, over time, into hyphae which in turn form mycelia. When the insect is inoculated via contact with the living propagules of the entomopathogenic fungi, the infection occurs as soon as the parasite relationship between the fungus and the target insect is established. With the development of infection, the fungus gradually kills the insect.

U.S. Pat. Nos. 5,057,316 and 5,057,315 disclose a method for control and extermination of insects, including roaches, flying insects such as the housefly, and other insects such as the adult form of the corn rootworm. The insects are controlled and exterminated by infection with a fungus that can be pathogenic when administered to the insects in a sufficiently high concentration, by means of an infection chamber. The chamber maintains the spores of a fungus pathogenic to the insects in a viable form, protecting the fungi from the environment (including rain, ultraviolet light and the wind), serves as, or houses, an attractant for the insects, and serves to inoculate the insects with high numbers of spores. The fungal culture provides a continuous supply of spores over a prolonged period of time. The spores attach to the insects and originate germ tubes that penetrate into the insect, which can result in death within three to four days. The chamber design, i.e., shape and color, can be the sole attractants for the insects. Alternatively, food or scents can be used to further enhance the attraction of the insects for the chamber. Although the primary means of infection is by external contact, the insects may also be infected by contact with each other and by ingestion of the spores. In some cases, the ingested fungal conidia can also be toxic.

A historical limitation on the commercial success of insect pathogenic fungi has been their lack of good storage characteristics. Although the chambers described in U.S. Pat. Nos. 5,057,316 and 5,057,315 have been demonstrated to be highly effective both in the laboratory and under actual field test conditions, it is necessary that they withstand shipping and be stable to prolonged storage at room temperature in order to constitute a viable commercial product.

The two most preferred entomopathogenic fungi are *Metarhizium anisopliae* and *Beauveria bassiana*. However, only limited success in commercialization of products of these two fungi has been achieved so far because of the obstacles encountered in stabilization, storage, and after-storage reactivation of fungal propagules such as conidia.

There is a series of six stages in the life history of a conidium: formation, maturation, after-ripening, activation, dormancy, and germination. In the dormancy stage, the spore is in a state of reduced physiological activity with an extended period of quiescence, and is most tolerant to the external environmental conditions. There are two types of dormancy: constitutive dormancy involves endogenous constraints that are not overcome simply by supplying conditions suitable for growth; exogenous dormancy is environmentally imposed, and ends when conditions suitable for growth are presented. Exogenous dormancy can be imposed either by withholding a special nutrient required for germination or by the presence of inhibitors, and can be maintained under certain environmental conditions.

It has been known for some time that dried microbial spores, cells, and other type of propagules may be preserved for longer periods of time than fresh ones. However, most scientists accept the generalization that dehydration of living cells may result in massive upheavals of membranes with irreversible loss of the structural and functional integrity (Crowe & Crowe, Stabilization of Membranes in Anhydrobiotic Organisms, In MEMBRANES, METABOLISM AND DRY ORGANISMS, A. C. Leopold, Comstock Publishing Co., Ithica, N.Y., pp. 188–209 (1986); Beker & Rapoport, Conservation of Yeast by Dehydration, In ADVANCES IN BIOCHEMICAL ENGINEERING/BIOTECHNOLOGY, Vol.35 of BIOTECHNOLOGY METHODS, ed. A. Fiechper, Springer Verlag, pp. 127–171 (1987)). This generalization is supported by the fact that there is a significant reduction of germination rate when spores or other types of microbial propagules are dried. Most research work on structural damage caused by dehydration has been focused on yeasts (Beker & Rapoport, 1987). Filamentous fungi produce different types of propagules, and conidium is the one that can be produced abundantly in a short period of time. However, conidia are not tolerant of dehydration. It has been found that conidia of various entomopathogenic fungi are very sensitive to drying processes and lose their viability very quickly (European Patent Application No. 92100010.5 by Eyal, et al.) Efforts have been made to develop mycelium formulations (Australia Patent Application No. P 36 39 508.8 by Andersch, et al.;), however, mycelial formulations are not stable at high temperatures, and have limited applications.

There are several studies on the effect of storage temperature and relative humidity (R.H.) on conidial stability and efficacy of *Metarhizium anisopliae* and *Beauveria bassiana* (Daoust & Roberts, Effect of Formulation on the Viability of *Metarhizium anisopliae* Conidia, *J. of Invertebrate Pathology*, Vol. 41, pp. 151–160 (1983); Walstad, J. D., "Effects of Environmental Conditions on Two Species of Muscardine Fungi (*Beauveria bassiana* and *Metarhizium anisopliae*)", *J. of Invertebrate Pathology*, Vol. 16, 221–226 (1970)). The results of these studies indicated that conidia of *M. anisopliae* survived the longest at moderate temperatures in the presence of high R.H. (26° C.+97% R.H. or 19° C.+97% R.H.). However, conidia lost their ability to germinate in a short period of time at 37° C. Germination is the first stage in the establishment of an entomopathogenic fungus.

During transportation and warehouse storage, the temperature could be as high as 37° C. No efforts have been made by the prior art to carefully investigate the status of the conidia that failed to germinate. Although techniques for accelerating and synchronizing germination of conidia of *M. anisopliae* have been studied by using fresh conidia materials. A period of 10 to 44 hours soaking in distilled water, and a suitable nutrient source are required (Dillon & Charnley, 1985). The conidia of entomopathogenic fungi, such as *M. anisopliae* and *B. bassiana*, are hydrophobic in nature. When they are suspended in water, the interface between water and the surface of conidia is characterized by the existence of a high surface tension which prevents the conidia from absorbing water necessary for germination. By carefully examining different surface active agents, it might be possible to alleviate this problem. Surface active agents are characterized by a structure in which the molecule is more or less clearly divided into distinct moieties. One moiety is hydrophilic, and the other hydrophobic. The method employed to quantify the hydrophilic-lipophilic nature of a surface active agent is Hydrophile-Lipophile Balance (HLB) method. In this method, an HLB number is assigned to each surface active agent, and is related by the scale to the suitable application surface active agent. The scale is devised so that the more hydrophilic surface active agents have higher HLB number. Although the HLB method for screening surface active agents has been used to chemical pesticide formulation, the application of HLB method in the screening of suitable surface active agents to reactivate microbial propagules after drying and storage is a new area. Moreover, little is known about the effect of $O_2$ levels on conidia viability when conidia are stored at different temperature-R.H. combinations. Oxygen is important for the germination of fungal spores.

It is therefore an object of the present invention to provide a method and means for increasing the shelf-life of a pathogenic fungus, especially *Metarhizium anisopliae*, on a nutrient medium.

It is a further object of the present invention to provide improved packaging for insect infection chambers utilizing a pathogenic fungus.

It is another object of the present invention to provide methods for storage to increase the shelf life of conidia of entomopathogenic fungi, at a higher temperature.

It is a further object of the present invention is to develop a suitable method to reactivate the conidia after storage.

SUMMARY OF THE INVENTION

Methods are described for packaging an infection chamber containing a fungal culture, or the conidia of the entomopathogenic fungi, especially of the genera Metarhizium. These methods permit the long term storage of conidia at a temperature of up to 37° C., and their subsequent reactivation for the control of insects such as cockroaches, flies, ants, soft-bodied insects, turf pests, caterpillars, etc., with little or no detectable loss in the ability of the fungus to infect and cause the death of susceptible insects.

Studies demonstrate that conidia of *Metarhizium anisopliae* maintained under atmospheric oxygen level (20% $O_2$) and high relative humidity (90–100% R.H.) at room temperature survive well, but lose viability in other R.H. and oxygen combinations at 37° C. Under conditions of a low oxygen level (0–5% $O_2$), 0–10% R.H. level, 56% and 26% of conidia were germinable after two months storage at 25° C. and 37° C., respectively. When the conidia of *M. anisopliae* were soaked in a suitable surfactant mixture, such as ethoxylated alcohol, with a hydrophile-lipophile balance (HLB) number of 10, germination rates at 25° C. and 37° C. were increased from 56% to 77% and from 26% to 74%, respectively. Conidia stored for two months under three different environmental conditions were tested in a bioassay to control wax moth, *Galleria mellonella*, larvae. The storage conditions were: (1) 90–100% R.H. and atmospheric oxygen level at 25° C., (2) 0–10% R.H. and 0–5% $O_2$ at 25° C., and (3) 0–10% R.H. and 0–5% $O_2$ at 37° C. The percentages of viable larvae treated with these three different groups of conidia show that the stored conidia were comparable or better than fresh ones. Packaging in low relative humidity provides an environment in which conidia dehydrate rapidly and assume dormancy status. The dehydrated conidia stored in low oxygen environment remain dormant during storage, and therefore survive well even at elevated temperatures. However, surface tension is increased by dehydration and germination is reduced after storage. The use of suitable surfactants reduced the surface tension of conidia and facilitated rehydration to break the dormancy.

Accordingly, in a preferred embodiment for packaging an infection chamber containing conidia, the packaging is made of gas-impermeable, water vapor-impermeable, flexible pouch material, such as aluminum foil and low density polyethylene-coated aluminum foil. The packaging ensures consistent oxygen and R.H. levels during storage. Desiccants can be used to create a low R.H., 0–10%, environment. A low-oxygen environment is created by packaging oxygen absorbers that can be used with desiccant into each pouch. A water agar plate can be used to maintain 90–100% R.H. A R.H. level of 35–40% can be provided by sealing the conidia in the packaging in the presence of air containing 35–40% R.H.

The conidia may be packaged with the desired oxygen and R.H. in a device such as an infection chamber. Conidia may also be packaged in bulk quantities under the appropriate conditions, and then suspended in a mixing tank for spray applications against pests. In this embodiment it may be desirable to include surface active agents that reduce the surface tension of fungal conidia to facilitate germination in an application vehicle without affecting the viability of the fungal conidia. After mixing the conidia with the application vehicle, the now fully-formulated fungal agent is ready for application using conventional devices and methods for spraying onto plants and other areas to be treated for insect control.

In a preferred embodiment for packaging an infection chamber containing fungal cultures, a flexible pouch material is provided that is water vapor impermeable and gas impermeable, and the fungal cultures are packaged in the presence of high humidity.

DETAILED DESCRIPTION OF THE INVENTION

Figure 1A:
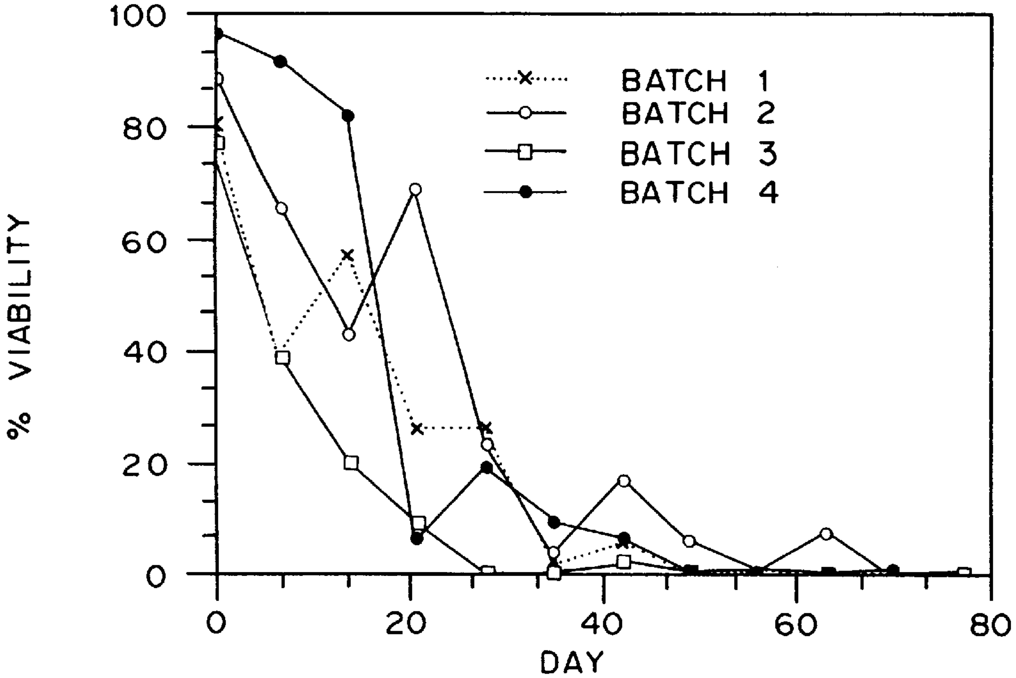
FIG. 1*a* is a graph of % viability of fungus within the infection chambers incubated under uncontrolled conditions over time (days), for four batches of *Metarhizium anisopliae*.

Methods of packaging are described for storing the entomopathogenic fungi, especially the genera Metarhizium, and its conidia. These methods permit the long term storage of the fungal conidia, and their subsequent use for the control of insects such as cockroaches, flies, ants, soft-bodied insects, turf pests, and caterpillars.

An essential element in the commercial development of a biological control system is that the agent must have a reasonable shelf life. The packaging systems used to ensure a reasonable shelf life must be economical and easy to assemble, transport, and store. The packaging must keep desirable fungal propagule types, such as conidia, viable and virulent under a reasonable temperature range.

The factors which appear to have the greatest importance in maintaining viability are relative humidity (R.H.), oxygen and temperature. As used herein, "low" R.H. means R.H. of less than 10%, or 0–10%, and "high" R.H. means R.H. of greater than 90%, or 90–100%. Median R.H. means 35–40%. Oxygen levels are generally in the range of atmospheric oxygen level, 20%, low oxygen level, 0–5%, or high oxygen level, 90–100%.

Storage Conditions for Fungal Cultures

In U.S. Pat. Nos. 5,057,315 and 5,057,316, the teachings of which are incorporated herein, a method for control and extermination of roaches and other insects using the dissemination of entomopathogenic fungi including, for example, *Metarhizium anisopliae* and *Beauveria bassiana*, was described. The fungi are applied to the environment to be treated using a contamination chamber consisting of a closed chamber having entrances for the insects and containing a living culture of a fungus pathogenic to insects. The geometry of the device is such that upon entering the chamber the insects come in contact with an effective dosage of the culture of the pathogenic fungus. It has been discovered that the fungus used in the insect infection chambers stores very poorly at room temperature in the absence of oxygen, regardless of the configuration of the chamber or storage container. Without continual access to oxygen, the fungus loses its viability, resulting in a chamber that is not efficacious in lethally infecting insects, although it is possible for the fungus to decline to 1% viability of the conidia in the chamber and still be efficacious. The fungus also has a requirement for high humidity. Increasing the storage temperature from room temperature, i.e., 22° C. to 25° C., up to 42° C. decreases the relative humidity requirements.

To meet both of these requirements, adequate oxygen and high humidity, a packaging material for the insect storage chamber, as well as the fungal cultures in general, has been designed which retains most of the water vapor while allowing free exchange of gases, including oxygen and carbon dioxide. The material is preferably impermeable to microbial organisms, including fungal spores, bacteria, and viruses.

Conditions are now described which allow for an extended shelf life for Metarhizium. These conditions are achieved by packaging the fungus under atmospheric gas and 100% RH. The packaging material is selected to allow the gases to reach an equilibrium while maintaining 100% RH.

Packaging Material

A variety of materials are commercially available which have defined characteristics with regard to their barrier properties; that is, their ability to contain or allow the movement of differing gases through a layer of the material. These materials come in both rigid and flexible formats. Pouches made of flexible barrier films are readily available in a variety of properties and configurations.

The most preferred material for packaging the chambers is 2 to 8 mil thick low-density and high-density polyethylene (referring to the extent of branching of the polymer) that can be sealed with heat. Other materials include polypropylene, which is slightly less permeable to air than polyethylene. As shown below, these commercially available materials are characterized by low water vapor transmission but high gas permeability.

TABLE 1

| | Properties of Packaging Materials for Fungal Cultures | | | | |
|---|---|---|---|---|---|
| | Water Vapor | Gas permeability[b] | | | Water |
| Material | trans[a] | $O_2$ | $N_2$ | $CO_2$ | absorption |
| Polyethylene (low density) | 1.3 | 550 | 180 | 2900 | low |
| Polyethylene (high density) | 0.3 | 600 | 70 | 4500 | low |
| Polypropylene | 0.7 | 240 | 60 | 800 | low |

[a]g loss/24 h/100 $in^2$/mil at 95° F., 90% R.H.
[b]cc/24 h/100 $in^2$/mil at 77° F., 50% R.H.; ASTM D1434-63

Other materials that are commercially available can be substituted for the polyethylene and polypropylene to provide equivalent gas and water vapor transfer. These materials can be obtained from D & B Plastics, Fairmouth, Minn., or other supplies of plastic sheeting.

Storage Conditions for Fungal Conidia

The fungal spore, the conidium, is not "inert" but consumes significant amounts of oxygen. This amount of oxygen, however, is much lower than that consumed by an actively growing fungal colony. Without access to oxygen, in the presence of high R.H., the conidium loses viability. However, conidia packaged with high R.H. and atmospheric oxygen levels at 25° C., lose their ability to germinate after two months of storage at 37° C. Studies have now been conducted that demonstrate that conidia maintain their viability in the presence of low R.H. (less than 10%) if the immediate environment is almost free of $O_2$ (0–5%). To meet the requirements of low oxygen and low relative humidity, a packaging material that is impermeable to any gas or water vapor is used in conjunction with a desiccant, and may be used in conjunction with a compound or process that removes oxygen.

Materials Used to Deplete or Remove Oxygen

There are a variety of oxygen depleting agents, such as oxygen absorbers, that can be packaged with the conidia. The oxygen absorbers used in removing oxygen in pouches or any other types of container, must be nontoxic to the fungal conidia. For example, Ageless™ is commercially available from the Mitsubishi International Corporation, Food division "B", 520 Madison Avenue, new York, N.Y. 10022. The major ingredient of Ageless™ is powdered active iron oxide which become iron oxides and hydroxides after absorption of oxygen. In an air-tight container, Ageless™ reduces oxygen down to 0.01% (100 ppm) or less. Oxygen absorbers selected also must be compatible with desiccants. Ageless™ Type Z, is especially suitable for use with dry materials, and can be used with desiccants. The capacity of the oxygen absorber to remove oxygen in a sealed container is another factor which should be considered. One bag of Ageless™-Z 300 has the capacity to absorb 300 ml of oxygen, which corresponds to an air volume of 1500 ml.

Alternatively, the oxygen can be removed from the package at the time of sealing by the application of vacuum, or by flushing the package with nitrogen before sealing.

Materials Used to Deplete or Remove Moisture

A variety of desiccants can be used to remove moisture from the packaging, for example, Drierite™, anhydrous calcium sulfate, is commercially available from W. A. Hammond Drierite Company, P.O. Box 460, Xenia, Ohio 45385. Drierite™ is a suitable desiccant that can be used in microbial pesticide packaging systems because it will not release any of its absorbed water when exposed to high ambient temperatures. The water is securely held in the form of the hemi-hydrate of calcium sulfate; which requires temperatures in excess of 350° F. (177° C.) to free the water. This is an important characteristic for shipping microbial products during variable weather conditions. For the drying of gases, Drierite™ has a water capacity of 10 to 14 weight percent. One Drierite™ desiccant bag will reduce the humidity in a sealed enclosure to a −100° F. (−73° C.) dew point in about 10 hours or less. One bag is used with a container of 24 cm×14 cm., having a volume of about 200–250 $cm^3$. Other compounds such as silica, certain clays, polyacrylic acid derivatives, and other desiccants may also be used to create a low R.H. environment.

Packaging Materials

In contrast to the materials used for packaging the fungal cultures, the material used to package conidia should be gas-impermeable. A preferred material for packaging conidia is polyethylene-aluminum foil-polyethylene having a thickness of at least 0.003 inches, most preferably 0.007 in., which is commercially available from Laminated Foil and Packaging, Portsmouth, N.H.

Other materials having an oxygen transmission rate of lower than 0.005 cc of 02/100 sq. inch per day and a vapor transmission rate below 0.005 cc of water vapor/100 sq. inch per day may be used. As used herein, materials having these transmission characteristics are considered to be "impermeable" to water and gases.

TABLE 2

| Properties of Polyethylene-aluminum Foil-polyethylene Bags for packaging conidia. | | |
|---|---|---|
| Thickness | Oxygen Permeability $O_2$ cc/100 $in^2$/24 h | Vapor Permeability $g/m^2/24$ h |
| 0.003" or 3 mil. | 0.005 | 0 |
| 0.005" or 5 mil. | 0.000 | 0 |
| 0.007" or 7 mil. | 0.000 | 0 |

Similar materials that are commercially available can be substituted for the laminated foil to provide equivalent gas and water vapor impermeability may also be suitable. These materials can be obtained from other suppliers.

Methods for Packaging the Fungal Culture and Conidia for Storage

The fungal culture or conidia are sealed within the pouch material using conventional methods known to those skilled in the art, such as heat sealing. Ultrasonic sealing can be used, but is not preferred. The conidia are sealed within the smallest pouch that will contain them, with no additional air or water being added at the time of the sealing, to the extent possible.

In a preferred embodiment, conidia packaged within gas-impermeable materials are packaged with a sufficient amount of a desiccant and an oxygen absorber to create conditions of less than 10% R.H. and less than 5% oxygen within the pouch. Alternatively, in a useful, but not preferred embodiment, conidia packaged within gas-impermeable materials are packaged with a limited amount of a desiccant to produce conditions of less than 10% R.H. within the pouch, omitting the oxygen absorbers.

The package can contain multiple compartments and means for mixing the contents of the compartments together. For example, to form a fungal propagule suspension for application to an area to be treated, a first compartment can contain a surface active agent while a second compartment contains fungal propagules. Similarly, to form a dry fungal propagule formulation, a first compartment can contain a dry surface active agent while a second compartment contains fungal propagules.

Surface Active Agents

Surface active agents, known as surfactants or wetting agents, can be employed to reactivate conidia after storage. Surface active agents can be divided into five principal classes: (1) anionic, (2) cationic, (3) non-ionic, (4) ampholytic, and (5) water-insoluble. In most cases, anionic and non-ionic agents are the preferred surface active agents. Each non-ionic surface active agent is assigned an HLB number within the scale on which that the more hydrophilic surface active agents have the higher HLB numbers. The HLB method is mostly applied in nonionic surfactant group, such as Iconol TDA, ethoxylated tridecyl alcohol, having an HLB of 10 (BASF Corporation, Persippany, N.J. 07054) seems to provide the best reactivation for the stored conidia of *Metarhizium anisopliae*. An HLB of 10 can be obtained by mixing Iconol TDA 6 (HLB=11) and Iconol TDA 3 (HLB=8) in a ratio of 2:1 (w/w/). Other non-ionic surface active agents by themselves or mixtures having HLB between 8–13, possessing different chemistry, such as block polymers; ethoxylated alcohols; ethoxylated alkyl phenols; ethoxylated amines and/or amides; ethoxylated fatty acids; ethoxylated fatty esters and oils (animal & vegetable); fatty esters; glycerol esters; glycol esters; lanolin-based derivatives; monoglycerides and derivatives; polymeric (polysaccharides, acrylic acid, acrylamide); propoxylated & ethoxylated fatty acids, alcohol or alkyl phenols; sorbitan derivatives; sucrose and glucose esters and derivatives, may be also used for this purpose. Some anionic and cationic surfactants having HLB in the range of 8–14 could also be used. For the anionic group or other groups, there are some surface active agents suitable for the reactivation of conidia, such as salts of sulfosuccinic acid, e.g., sodium dioctyl sulfosuccinate, salts of sulfonic acid, e.g., dodecyl benzene sulfonate, salts of naphthalene sulfonates, and taurates (Igepon T-77). Examples of these surface active agents include: block polymers, e.g., Pluronic 25R4; Ethoxylated alcohols, e.g., Tergitol 15 S-5; Ethoxylated alkyl phenols, e.g., Triton N-57.; Ethoxylated amines and amides, e.g., Ethomid O-17; Ethoxylated fatty acids, e.g., PEG oleate; Ethoxylated fatty esters and oils, e.g., Alkamuls EL-620; Glycerol esters, e.g., Emerest 2421; Glycol esters, e.g., Ethox DO-9; Polymeric polysaccharides, acrylic acid, and acrylamide, e.g., APG 325 Glycoside; propoxylated and ethoxylated fatty acids, alcohol or alkyl phenols; sorbitan derivatives, e.g., Span 60; and sucrose and glucose esters and derivatives, e.g., Crodesta F-50. Examples of anionic surface active agents include salts of sulfosuccinic acid (e.g., dioctyl sulfosuccinate), salts of sulfonic acid (e.g., salts of dodecyl benzene sulfonate, sodium salts of alkylnaphthalene sulfonate), phosphate esters, and taurates.

The HLB numbers of surface active agents are preferably within the range of 9–11 for *M. anisopliae*. The HLB numbers of surface active agents are preferably within the range of 9–14 for *Beauveria bassiana*.

The amount of surfactants, i.e., one or a mixture of surfactants, needed to reactivate the conidia can be as low as 0.01 to 100% (w/w) (i.e., in ratios ranging from 1:1000 to 100:1) that of conidia depending on the surfactant(s) being used. Review of the HLB values in screening surface active agents is preferred since once a suitable HLB number is determined other different surface active agents with the same HLB number that are not harmful to the corresponding type of fungal propagules, bacterial cells or other microorganisms may also be used in reactivating conidia.

In a preferred embodiment, conidia are packaged in foil with a sufficient amount of a desiccant to produce low R.H. within the package, and a sufficient amount of an oxygen absorber to create low oxygen environment within the package. This package is then mixed with the contents of a second package containing the surface active agent mixture or a suspension of the mixture, to reactivate the conidia before application. Moreover, the preferred surface active agents, if necessary, can be mixed with the conidia and some inert materials as a final formulation and stored as described above. The conidia, later mixed with the surface active agent or the formulated material containing the conidia and the surface active agents, can be applied as a spray, dust, tablet, granules or gels. For example, two components of the final formulation, i.e., conidia and surfactant mixture, can be packaged separately, and mixed up before application. The now fully-formulated fungal agent can then be applied as a spray, drench, or dust application against insects such as cockroaches, whiteflies, aphids, termites, or ants.

The present invention will be further understood by reference to the following non-limiting examples demonstrating the importance of various features of the method and packaging materials.

The following materials and methods were used to determine the effect of various storage conditions on viability and efficacy of the fungal culture in the following examples.

Viability

The percent viability (germination) of *M.anisopliae* (*M.a.*) conidia was determined using Potato Dextrose Agar (PDA) Plates according to the following procedure:

Obtain a fresh, sterile plate of PDA. Collect conidia by gently touching the tip of a small sterile paintbrush to the conidial lawn. Touch brush tip to the inside of a sterile petri dish to remove excess conidia. Only a small amount of conidia are needed. Carefully and gently brush the conidia onto one quarter of the PDA plate, repeat for the other three quarters using conidia obtained from different areas of the Metarhizium source. One or two brush strokes per quarter is sufficient. Incubate petri dishes at 28° C. for 11–13 hours. After 13 hours of incubation, examine the surface of each inoculated area at 200 power under the compound microscope. Find a field that allows examination of individual conidia. Count at least 200 conidia and record the number of viable and non-viable conidia. A viable conidium has a germ tube at least as long as the diameter of the conidia. For each inoculated quarter obtain the number of viable conidia/total conidia counted, average the four counts together and multiply by 100 to determine the percentage of viable conidia.

Efficacy

For examples 1 through six, efficacy was determined using *Blatella germanica* in a shoe box bioassay.

Materials

Polystyrene shoe storage boxes (12.5×6.75×3.6 inches) having air holes in the top covered with Polyester mosquito mesh netting.

Adult German cockroaches (*B. germanica*; JK-Consulting, Amherst, Mass.), fed Purina Lab Chow (Purina #5001; Purina Mills, Inc., St. Louis, Mo.), with free access to distilled water in a test tube-stoppered with tissue.

Environmental chamber with controlled temperature and humidity and continuous data recorder (28° C. and 75% R.H.), into which the shoe boxes were placed.

Methods

Vertical sides of shoe boxes were coated with a thin layer of petroleum jelly. A pellet of autoclaved Purina Lab Chow and a water tube were added to each shoe box. Twenty cockroaches were added to each box. The shoe boxes of cockroaches were placed in the environmental chamber. One infection chamber as described in U.S. Pat. Nos. 5,057,315 and 5,057,316 was added to each of four shoe boxes of cockroaches. Four additional shoe boxes were used as controls.

Shoe boxes of cockroaches were incubated at 28±3° C. and 75±15% R.H. under a 10 hour photoperiod. Cockroach mortality was recorded weekly for 6 weeks. The criteria for 'dead' was if no movement was observed when the insect was prodded with a blunt instrument.

EXAMPLE 1

Loss of Fungal Viability when Chambers are Left Unprotected at Room Temperature and with Uncontrolled Humidity Chambers from four different batches of fungus were placed inside a cabinet at room temperature and humidity. At intervals measured in days, chambers were sampled and the viability of the fungus determined.

The results shown in FIG. 1*a* indicate that fungus loses viability when stored unprotected over any significant period of time.

EXAMPLE 2

Effect on Fungal Viability When Chambers are Stored Under Anaerobic Conditions

Five infection chambers were placed in each of a series of one quart mason jars which can be fitted with an air tight lid. For those chambers which were the controls and exposed to atmospheric conditions, the jar lid was left loose. For those chambers which were to be exposed to anaerobic conditions, an Ageless™ (Mitsubishi) oxygen scavenger pack was introduced, and the jar lid was tightened down. An Ageless™ pack consists of finely divided, un-oxidized iron filings, which when exposed to air begin to oxidize. When this occurs in a sealed environment, such as these jars, all oxygen is removed, creating an anaerobic environment.

Figure 1B:
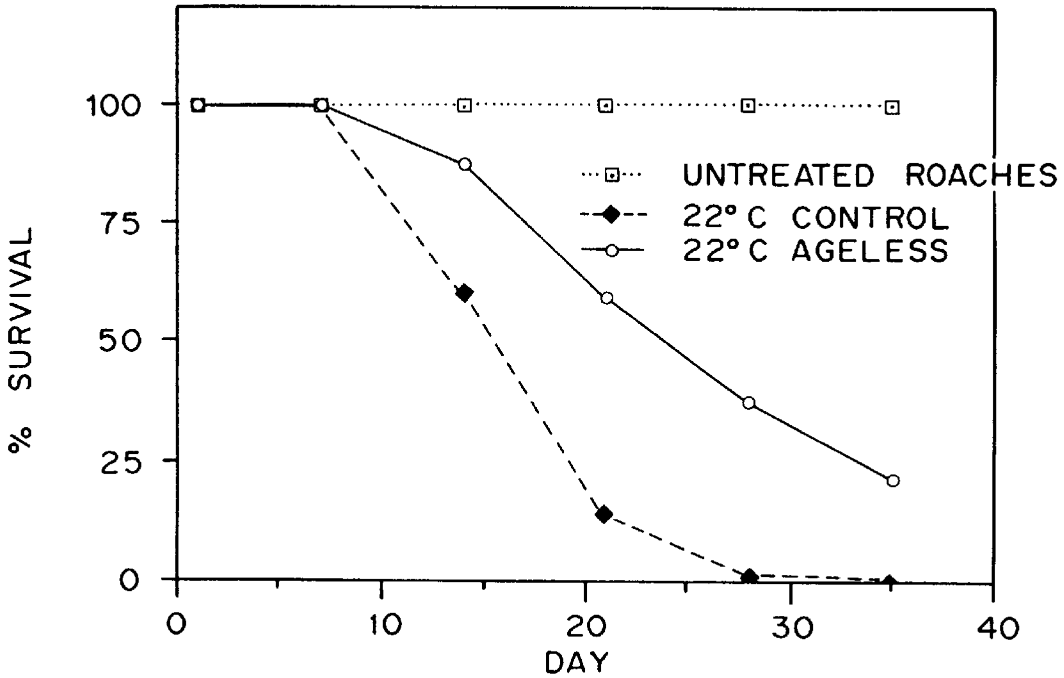
FIG. 1*b* is a graph of the % survival of roaches exposed to infection chambers containing fungus which had been stored under aerobic (—dark diamonds—) or anaerobic (—O—) conditions over time (days). Survival of roaches not exposed to fungus are shown as (· · · open squares· · ·).

The data shown in Table 3 and FIG. 1*b* illustrate the average viability as well as the efficacy of the infection chambers after storage for 42 days under these conditions. The results demonstrate that oxygen is a requirement for successful long-term storage of the fungus at room temperature at normal atmospheric humidity.

TABLE 3

Viability of Fungus Inside Infection Chamber.

| | | % Viability |
|---|---|---|
| 14 days | Control | 72.06 |
| | Ageless | 69.94 |
| 42 days | Control | 81.54 |
| | Ageless | 7.00 |

EXAMPLE 3

Determination of Suitable Packaging Materials for Fungal Culture, Allowing Flux of Oxygen Several materials were tested to determine how the live fungus within the infection chamber consumes oxygen, and how, when the fungus is packaged, different packaging materials do or do not mitigate the oxygen feficit by allowing the passage of oxygen.

Two studies were performed:

1) Six chambers with fungus were placed into either: (a) a Rubbermaid™ container (7.5 in×7.5 in×2.75 in), (b) and a 4 mil (0.004 in) low-density polyethylene pouch (LDPE) (D&B Plastics, Fairmouth, Minn.), or c) an 8 mil LDPE pouch. There were duplicate samples of each, designated "A" and "B". While Rubbermaid™ containers are made of thick polypropylene, a low oxygen permeable material, oxygen transfer can occur around the seal of the lid to the container. As shown in Table 1, LDPE is noted for its low water vapor permeability characteristics and its high oxygen and carbon dioxide permeability characteristics.

The packaged chambers were stored at 30° C. for fourteen days. At the end of this period, the oxygen and carbon dioxide content of the package interiors was sampled using a Servomex™ Company, Norwood, Ma., gas analyzer. The average viability of the fungus within the chambers was then determined. The results are shown in Table 4.

TABLE 4

Conditions inside Packages with Infection Chambers after 14 Days at 30° C.

| | | % $O_2$ | % $CO_2$ | % Viability |
|---|---|---|---|---|
| Rubbermaid ™ | A | 16.0 | 5.5 | 95.0 |
| | B | 11.4 | 10.4 | 92.2 |
| 4 mil LDPE | A | 12.5 | 2.2 | 86.3 |
| | B | 12.3 | 2.3 | 86.1 |
| 8 mil LDPE | A | 5.9 | 3.8 | 93.0 |
| | B | 5.0 | 4.0 | 94.1 |

2) Twelve chambers were sealed inside each of several foil laminate pouches (Laminated Foil and Packaging, Portsmouth, N.H.). The laminations were polyethylene-aluminum foil (0.0007 inch)-polyethylene; this packaging material is considered completely impermeable to any gas or vapor. The pouches were stored and their oxygen and carbon dioxide levels were subsequently measured. There were duplicate pouches for each sampling point.

The results are shown in Table 5 and demonstrate that all of the oxygen was consumed and carbon dioxide was produced in abundance. The average viability of the fungus was then determined.

TABLE 5

Conditions inside Foil Pouches after Three Months.

| | | % $O_2$ | % $CO_2$ | % Viability |
|---|---|---|---|---|
| 22° C. | A | 0.3 | 23.4 | 15.0 |
| | B | 0 | 22.9 | 11.15 |
| 30° C. | A | 0 | 23.7 | 0.0 |
| | B | 0 | 22.0 | 0.25 |

The results of these two experiments demonstrate the extent of oxygen consumption by the fungus, and, when combined with the other examples, demonstrate the importance of providing the appropriate packaging. Fungus with access to oxygen remains viable.

EXAMPLE 4

Importance of High Humidity on Storage Stability of the Fungus

Five infection chambers with fungus were placed inside each of a series of Rubbermaid™ containers to determine the role that the relative humidity (R.H.) within the container had on the long-term storage stability of the fungus. One series of containers had placed inside of them a wet sponge to insure the container atmosphere was kept at 100% R.H. Another series of containers had a saturated solution of magnesium chloride ($MgCl_2$) placed within to maintain 30% R.H. A final series of containers was kept at 0% R.H. by placing inside of them a large amount of silica gel. All of the containers were stored at room temperature, and the infection chambers within the containers were sampled periodically to determine fungal viability and chamber efficacy over an extended period of time.

Figure 2:
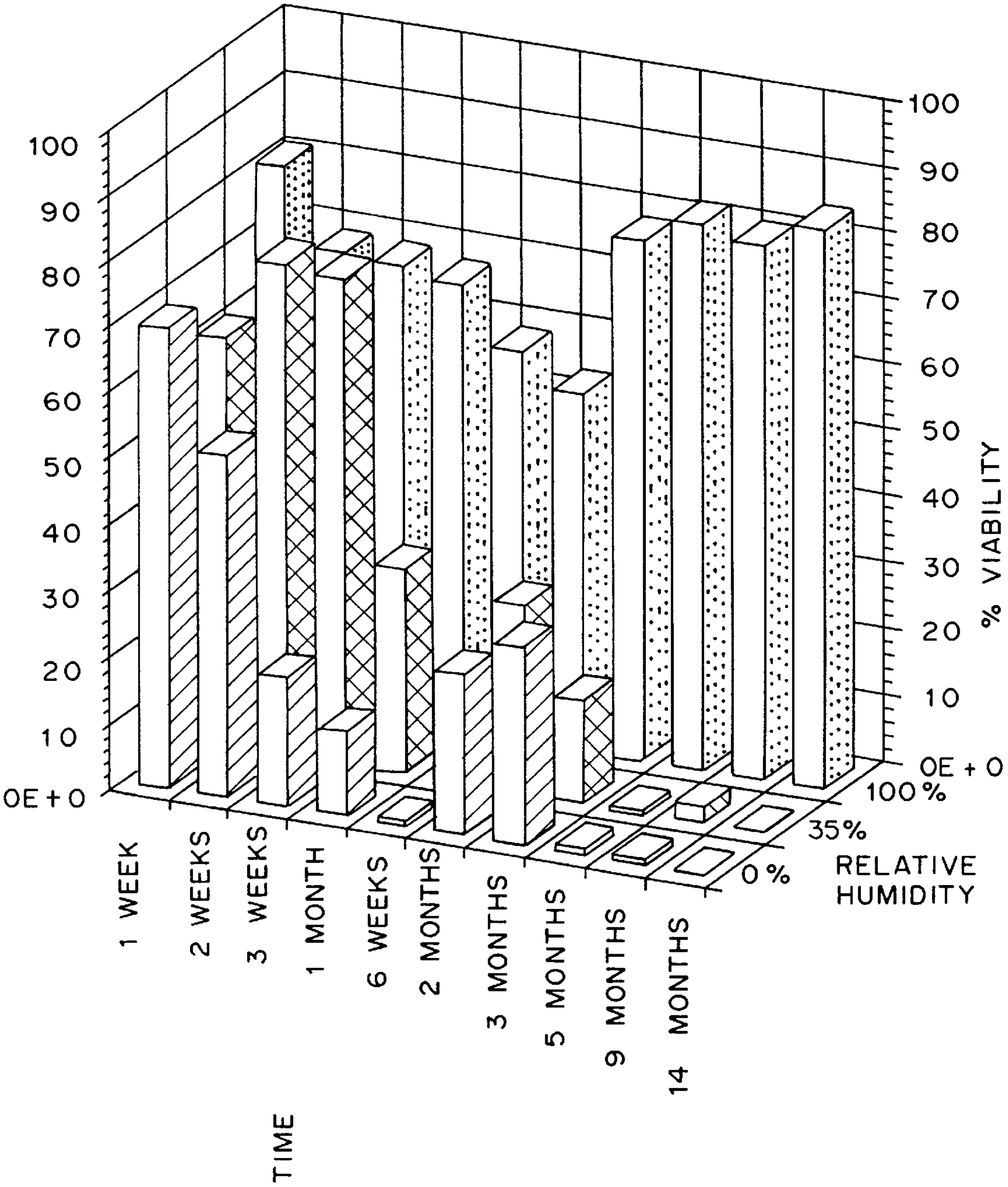
FIG. 2 is a three dimensional graph of the viability of fungus within infection chambers incubated at different relative humidities: % viability versus % relative humidity versus time.
Figure 3:
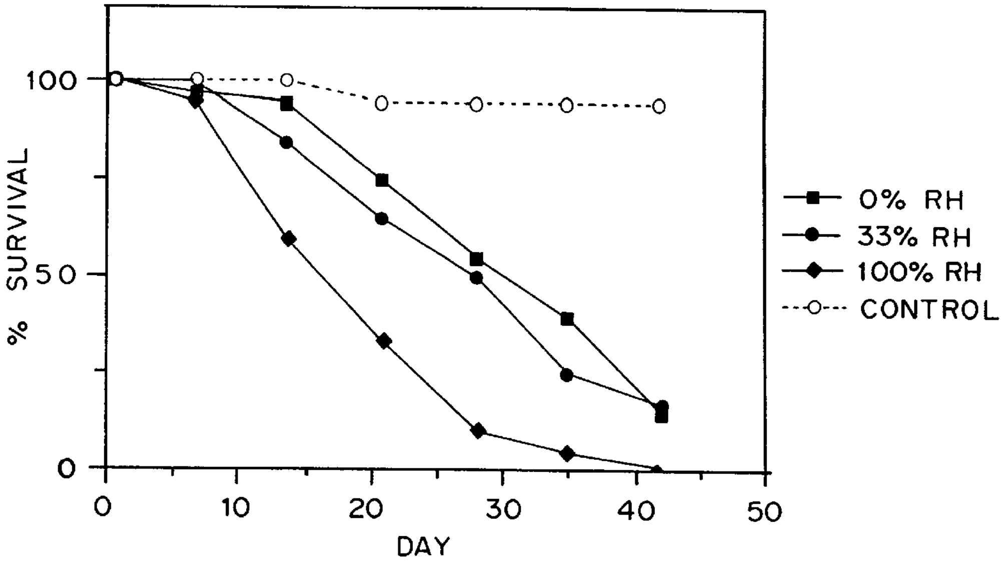
FIG. 3 is a graph of % survival of cockroaches (*Blatella germanica*) over time (days) exposed to infection chambers containing Metarhizium anisopliae cultures, stored at 0% R.H. (dark squares), 33% R.H. (dark circles), 100% R.H. (dark diamonds), and controls (open circles) at 22° C.

The results are shown in Table 6 and in FIG. 2. These result show the average measured viability in tabular and graph form through 14 months of storage. The efficacy of the infection chambers at 9 months is also shown in FIG. 3.

The results demonstrate that 100% R.H. is significantly better than other humidities for the successful long -erm storage of the fungus.

TABLE 6

Percentage Viability at Various Relative Humidities.

| | Relative Humidity of | | |
|---|---|---|---|
| Time | 100% | 33% | 0% |
| 1 week | 81 | 61.1 | 69.1 |
| 2 weeks | 69 | 74 | 51 |
| 3 weeks | 68.5 | 73.1 | 19.2 |
| 1 month | 67.3 | 30.5 | 12.7 |
| 6 weeks | 58.4 | 11.4 | 0.54 |
| 2 months | 53.5 | 28 | 23.9 |
| 3 months | 78.3 | 15.3 | 29.8 |
| 6 months | 82.33 | 0.08 | 0.74 |
| 9 months | 80.54 | 2.33 | 0.75 |
| 14 months | 84.29 | 0 | 0 |

EXAMPLE 5

Comparison of Different Commercial Packaging Materials in their Ability to Provide Suitable Long Term Storage Conditions for the Fungus Twelve infection chambers were placed into each pouch of two series of pouches. One pouch series was 8 mil LDPE. The other pouch series was a foil laminate, as in Example 3. Pouches were stored at either 22° C. or 30° C. The required 100% R.H. within the pouch was provided by the agar growing medium of the fungus which remains within the chamber after development of the fungus. At periodic intervals the pouches were removed from their storage conditions and initially sampled for gas content. Each sample consisted of duplicate pouches (A and B). The results obtained were consistent with the data obtained in Example 3; that is, within a short period of time, there was no oxygen remaining in the foil laminate pouches but there was a substantial amount within the LDPE pouches. The pouches were then opened, and the chambers within were sampled for viability of the fungus. The results show that at three months, a clear distinction emerges between an oxygen-permeable (LDPE) pouch and an oxygen-impermeable (foil) pouch.

It can be concluded that the fungal culture requires oxygen, and that a LDPE bag allows sufficient exchange to maintain the viability of the fungus over long term storage.

TABLE 7A

Conditions within Foil Pouch at Three Months.

| | | % $O_2$ | % $CO_2$ | % Viability |
|---|---|---|---|---|
| 22° C. | A | 0.3 | 23.4 | 15.00 |
| | B | 0 | 22.5 | 11.15 |
| 30° C. | A | 0 | 23.7 | 0.00 |
| | B | 0 | 22.0 | 0.00 |

TABLE 7B

Conditions within LDPE Pouch at Three Months

| | | % $O_2$ | % $CO_2$ | % Viability |
|---|---|---|---|---|
| 22° C. | A | 8.5 | 3.0 | 92.1 |
| | B | 8.8 | 2.5 | 90.9 |
| 30° C. | A | 8.7 | 3.0 | 86.0 |
| | B | 4.5 | 4.2 | 87.8 |

EXAMPLE 6

Comparison of Packaging Conditions on Viability of Different Fungi

Figure 4A:
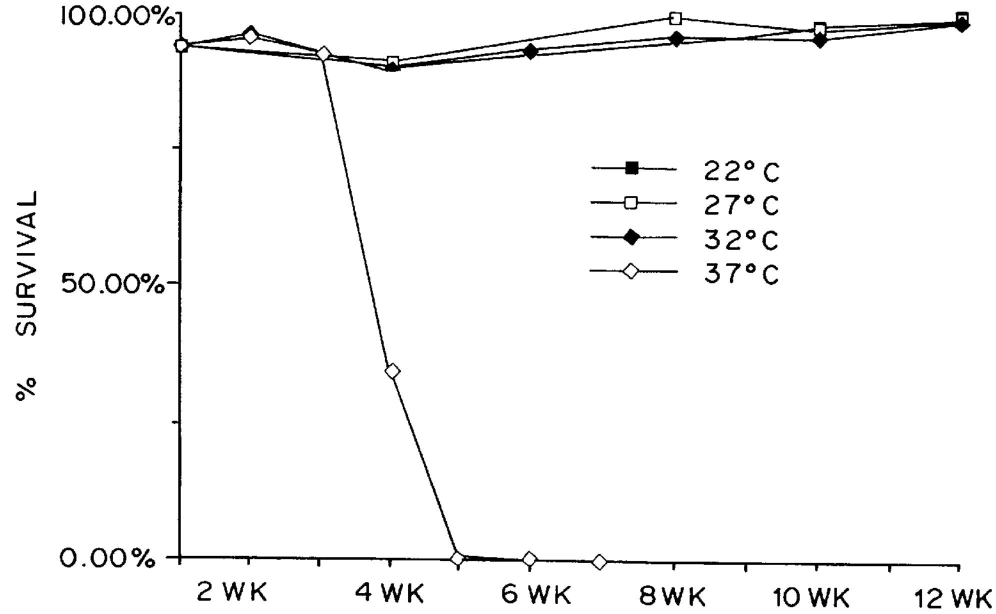
FIGS. 4*a*, 4*b*, and 4*c* are graphs of the % survival over time (weeks) for *M. anisopliae* strain ESF 53 (FIG. 4*a*), *M. anisopliae* strain ESF 1 (FIG. 4*b*), and *Beauveria bassiana* strain ESF 2 (FIG. 4*c*) at 22° C. (dark squares), 27° C. (open squares), 32° C. (dark diamonds), and 37° C. (open diamonds).
Figure 4B:
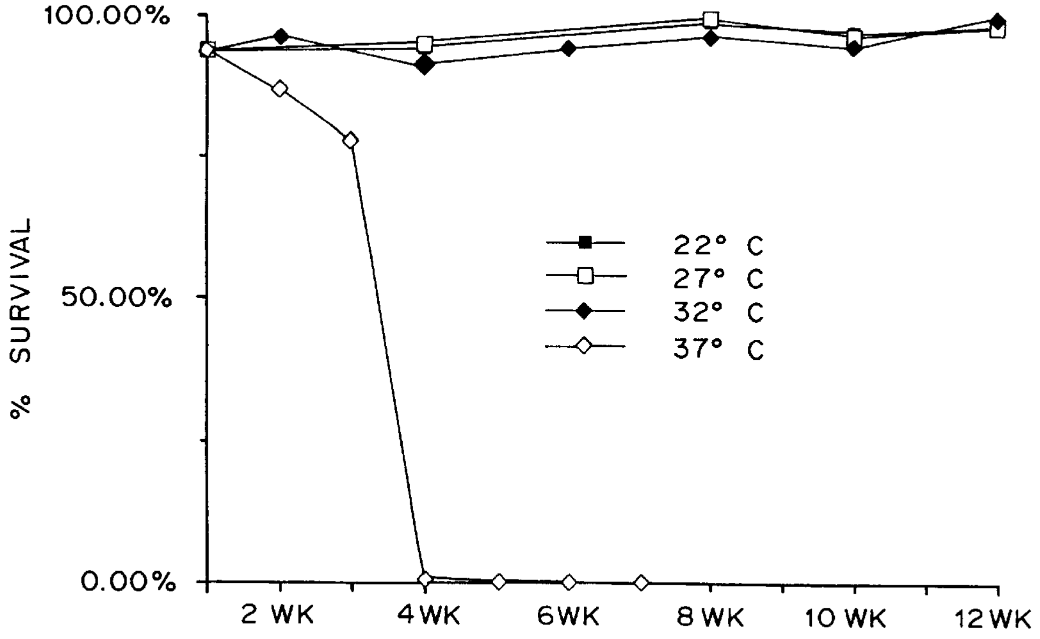
Figure 4C:
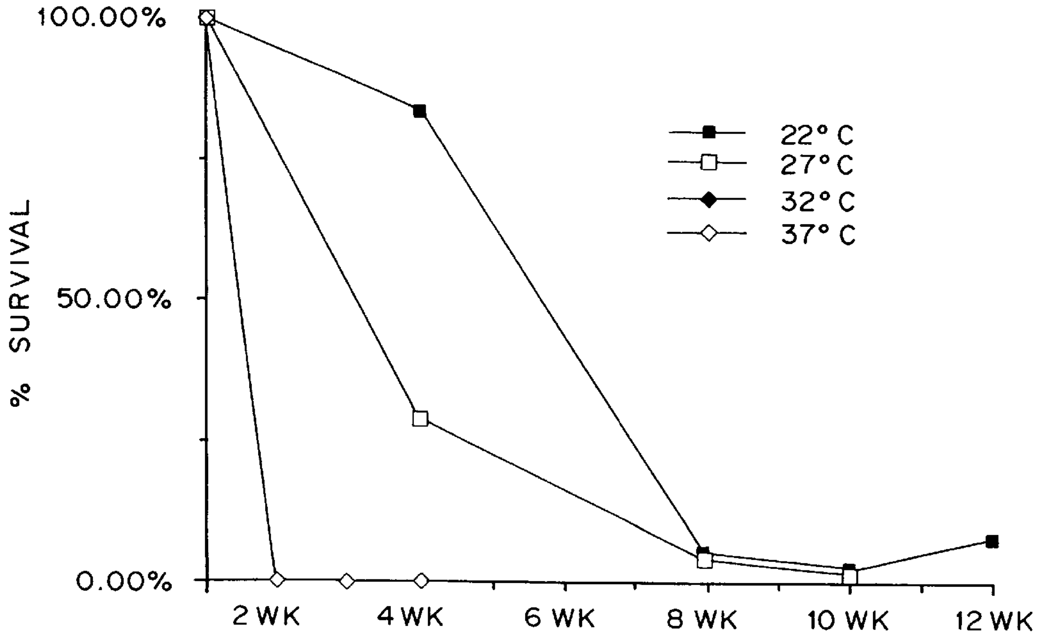

FIGS. 4*a, b* and *c* demonstrate the percent survival over time for three different fungi stored under conditions as described in Example 3. Strain ESF 2 is a *Beauveria bassiana* strain, and strains ESF 1 and ESF 53 are strains of *Metarhizium anisopliae* strains.

Under the same conditions, the *Beauveria bassiana* strain does not survive well using the same packaging material that preserves both *Metarhizium anisopliae* strains. These results indicate that it is not possible to extrapolate from data on packaging of other types of microorganisms to fungi with respect to the efficacy of the packaging in promoting survival of fungi.

EXAMPLE 7

Determination of the Effects of Various Storage Conditions on Viability and Efficacy of a Fungal Conidia The following materials and methods were used to determine the effect of various storage conditions on viability and efficacy of the fungal conidia.

Viability of *B. bassiana* or *M. anisopliae* conidia was determined by streaking conidia stored in each pouch (replication) onto Potato Dextrose Agar (PDA) plate as described above. Conidia of *B. bassiana* on PDA plate are incubated for 18 hours at 22° C., and *M. anisopliae* for 15 hours at 25° C. After incubation, the number of germinated conidia on each of the PDA plates is counted. Viability of each replication is expressed as the percent germination. The average percent germination of each treatment is then calculated from four replications and presented with standard deviation.

Strain ESC-1 of *M. anisopliae* and ESC-170 of *B. bassiana* were employed, and the fungal propagule type used was conidia kept in a small weighing pan. The type consisted of conidia which had been "brushed" off the mycelial layer and placed in a weighing pan. Ageless™ was used to create an immediate low oxygen (<5%) environment. The Ageless™ Type Z-300 was used because it is especially suitable for dry materials and can be used with desiccants. One bag of Ageless™-Z 300 has the capacity to absorb 300 ml of oxygen which corresponds to an air volume of 1500 ml. The volume of the foil pouch (bag) was approximately 250 ml. High R.H. was maintained within certain pouches during the experiment by the water vapor generated from the water agar plate devoid of fungus, and not in direct contact with the conidia. Drierite™ was used to reduce the R.H. levels in certain pouches to less than 10%. A one ounce bag of Drierite™ was packed into each pouch that required a lower R.H. environment. There was no air exchange in the foil pouches.

All treatments were incubated at 25° C. and 37° C. for either four or eight weeks. Each treatment had 4 replications, and the mean of four replications was presented with the standard deviation.

Figure 5:
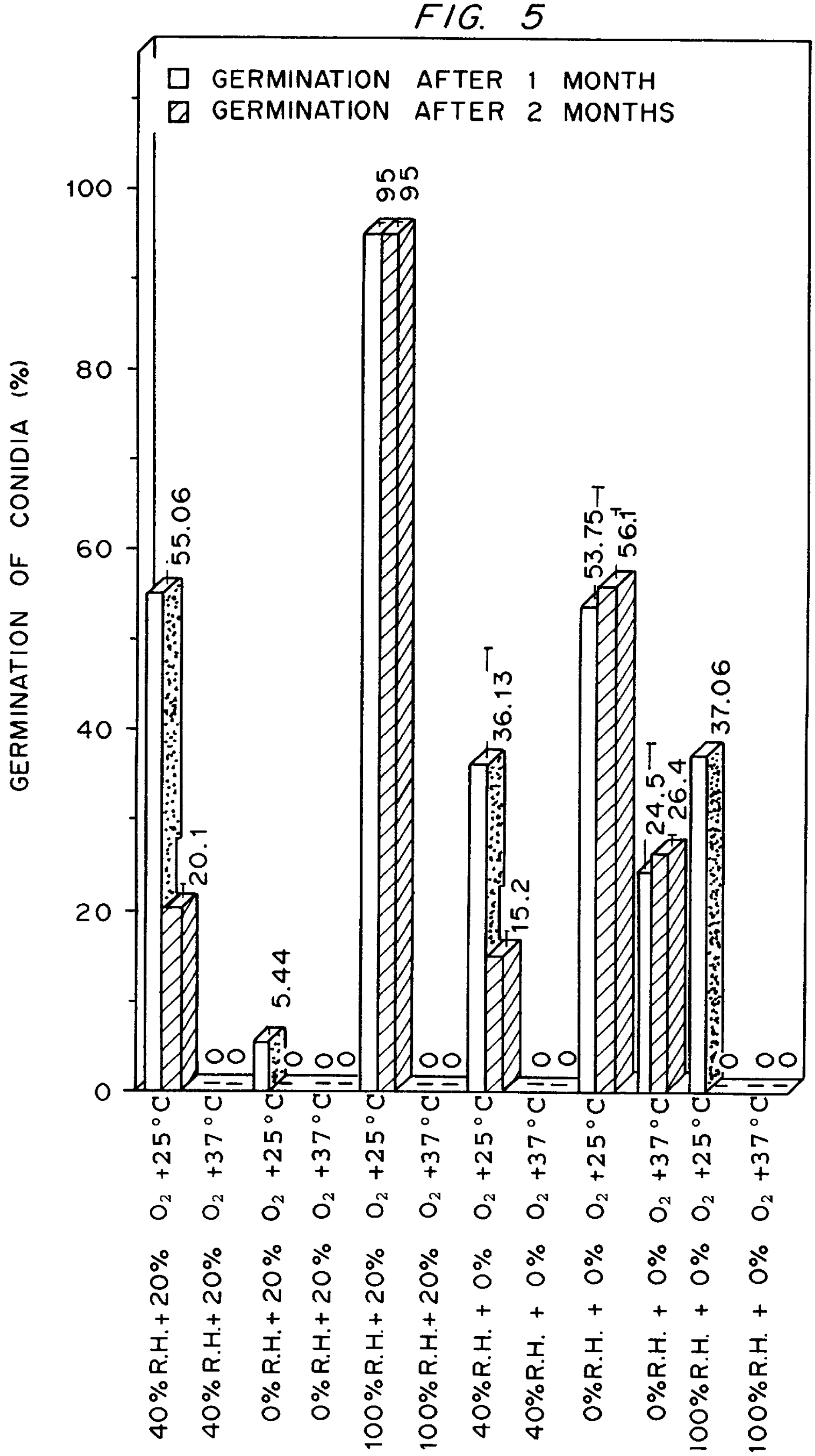
FIG. 5 is a graph of percent germination of *M. anisopliae* conidia versus packaging systems that create various storage conditions at both 25° and 37° C. for a period of one and two months. The packaging systems were foil alone, foil+ Drierite™, foil+water agar, foil+Ageless™, foil+ Drierite™+Ageless™, foil+water agar+Ageless™. Conditions (from left to right) were: 40% R.H.+20% $O_2$ at 25° C.; 40% R.H.+20% $O_2$ at 37° C.; 0% R.H.+20% $O_2$ at 25° C.; 0% R.H.+20% $O_2$ at 37° C.; 100% R.H.+20% $O_2$ at 25° C.; 100% R.H.+20% $O_2$ at 37° C.; 40% R.H.+0% $O_2$ at 25° C.; 40% R.H.+0% $O_2$ at 37° C.; 0% R.H.+0% $O_2$ at 25° C.; 0% R.H.+0% $O_2$ at 37° C.; 100% R.H.+0% $O_2$ at 25° C.; and 100% R.H.+0% $O_2$ at 37° C.

The results are shown in FIG. 5 for *Metarhizium anisopliae* at atmospheric oxygen level (20% $O_2$). Conidia of *M. anisopliae* are less stable then those of *B. bassiana*. Although they survived well when packaged under normal atmospheric oxygen level and 90–100% R.H. at 25° C., they lost viability in other R.H. and oxygen combinations at 37° C. Packaged under 0–5% oxygen and 0–10% R.H. level, 56% and 26% of conidia were germinable after 2 months storage at 25° and 37° C., respectively.

EXAMPLE 8

Determination of the Suitable Surface Active Agent for Reactivating Stored Dry Conidia of *M. anisopliae*

Surface active agents of different chemistries and HLB ratings were screened based on the effect of percentage germination.

100 ml of surface active agent solutions/suspension with a certain HLB number or chemistry was placed in a 250 ml beaker. 0.01 g to 0.5 g of dried conidia was dusted onto the surface of the solution or suspension of the surface active agent. Once the conidial sample was wetted in the surfactant solution, the solution was transferred to a 100 ml graduated cylinder and mixed by inversion (30 times in one minute). Conidia were allowed to settle to the bottom of the graduated cylinder at room temperature. The supernatant was decanted and the sedimented conidia were sampled with a sterile cotton swab. PDA plates were then inoculated with each conidial sample, incubated at 25° C. for 25 hours, and the number of germinated conidia per 100 total conidia was determined.

Figure 6:
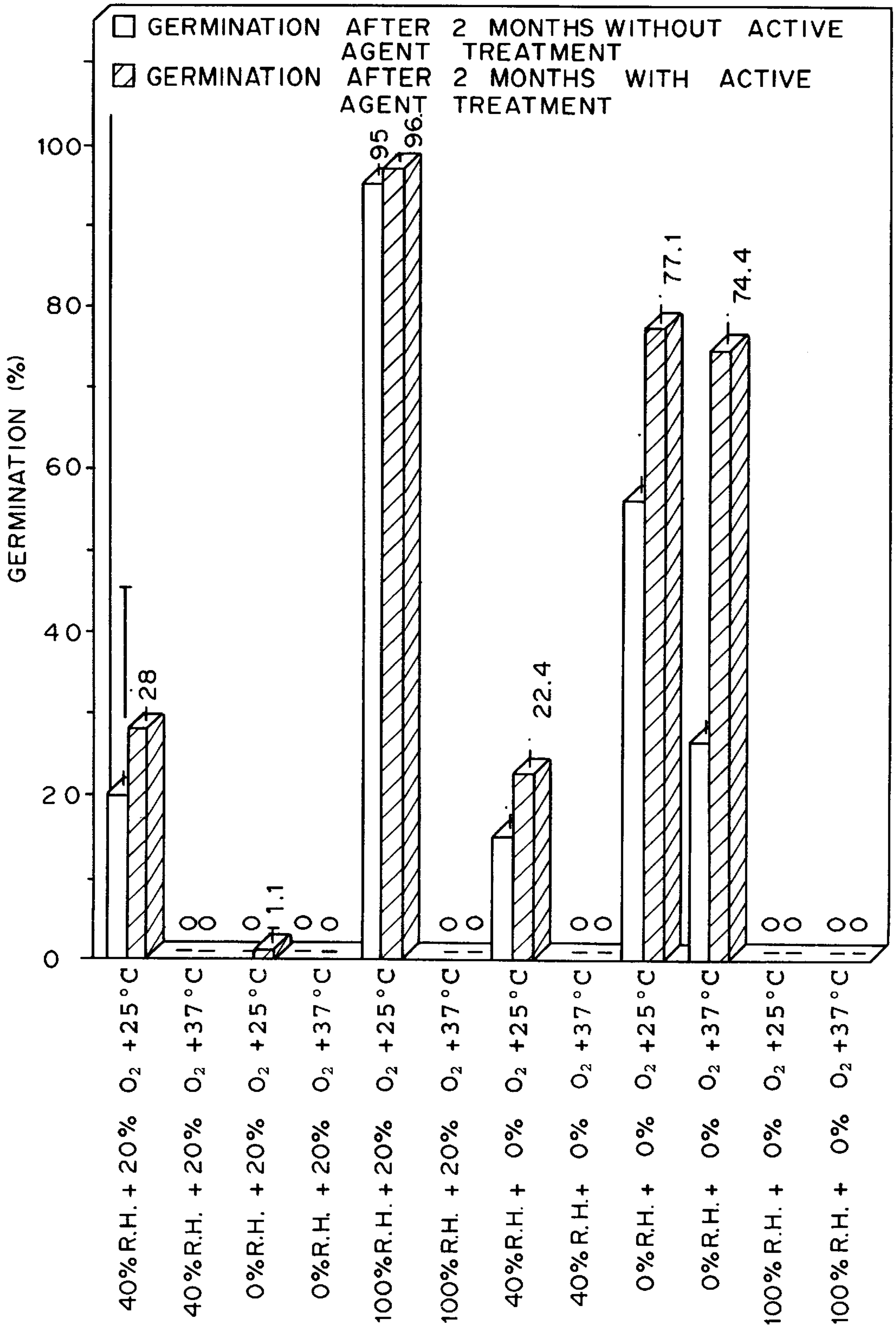
FIG. 6 is a graph of percent germination of *M. anisopliae* conidia versus packaging systems that create various storage conditions at both 25° C. and 37° C. for 2 months, determined with or without surface active agent treatment after storage. The packaging systems were foil alone, foil+ Drierite™, foil+water agar, foil+Ageless™, foil+ Drierite™+Ageless™, foil+water agar+Ageless™. The surface active agent used was ethoxylated tridecyl alcohol. The storage conditions were the same as described in FIG. 5.

The results are shown in Table 8 and in FIG. 6. FIG. 6 is a graph of percent germination of *M. anisopliae* conidia versus packaging systems that create various storage conditions at both 25° C. and 37° C. for 2 months, determined with or without surface active agent treatment after storage. The packaging systems were foil alone, foil+Drierite™, foil+water agar, foil+Ageless™, foil+Drierite™+Ageless™, foil+water agar+Ageless™. The surface active agent used was ethoxylated tridecyl alcohol, with a hydrophile-lipophile balance (HLB) number of 10. Conidia were vortexed for 10 seconds and soaked for 15 minutes in this surface active agent.

TABLE 8

Effect of Soaking Conidia in 0.05% (w/v) Ethoxylated Tridecyl Alcohol Solution with an HLB of 10 on the Reactivation of Stored Dry Conidia of *M. anisopliae.*

| Treatment | % Germination | Standard Deviation |
|---|---|---|
| Dried Conidia, Control | 20.6 | 2.7 |
| Dried Conidia vortexed for 10 seconds with Iconol TDA | 88.2 | 2.8 |
| Dried conidia vortexed for 10 seconds with Iconol TDA plus 15 minutes of soaking | 85.8 | 5.3 |
| Dried conidia vortexed for 10 seconds with Iconol TDA plus 6 hours of soaking | 84.7 | 3.5 |

The results clearly demonstrate that when the conidia of *M. anisopliae* were soaked in a suitable surfactant, such as ethoxylated tridecyl alcohol, with a hydrophile-lipophile balance (HLB) number of 10, the germination rates were increased from 56% to 77% and from 26% to 74%, respectively.

EXAMPLES 9

Determination of Efficacy of Stored Conidia in a Bioassay.

Efficacy of stored conidia was tested in a bioassay to control wax moth, *Galleria mellonella*. The last instar larvae of wax moth were supplied by Northern Bait, 1520 Knapp St., P. 0. Box 216, Chetek, Wis. 54728.

Wax moth last instar larvae were dipped in previously stirred suspensions of conidia in small beakers and held for 15 seconds. Groups of 10 insects were treated together in a tea strainer and placed in 100 mm plastic petri dishes with vermiculite moistened with 1 ml of deionized water. Mortality was scored after 4 days, and after 11 days. All were held for an additional week and scored for external conidiation.

Figure 7:
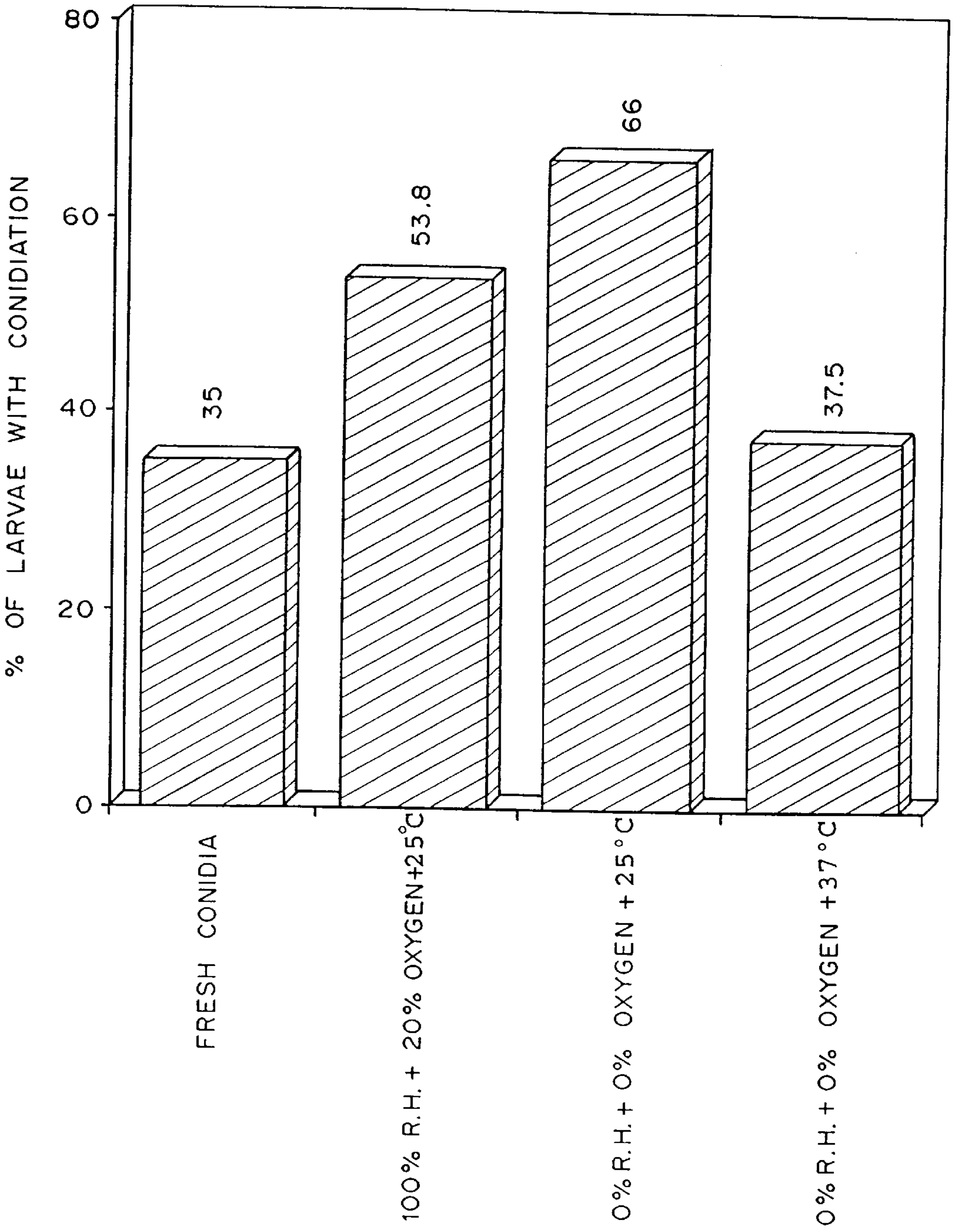
FIG. 7 is a graph of external conidiation on wax moth, *Galleria mellonella*, larvae treated with conidia of *M. anisopliae* stored under different environment conditions of two months. The conidia were (1) fresh; packaged (2) with a water agar plate to keep 100% R.H., and stored at 25° C., (3) with Drierite™+Ageless™, and stored at 25° C. or (4) 37° C. The larvae with newly formed conidia on their bodies were recognized as larvae with conidiation. Mortality in all treatments were 100%.

Conidia stored under three different environment conditions were tested in a bioassay to control wax moth, *Galleria mellonella*, larvae. The conditions were as follows: (1) 90–100% R.H. and atmospheric oxygen level at 25° C., (2) 0% R.H. and 0–5% oxygen at 25° C., and (3) 0% R.H. and 0–5% oxygen at 37° C., for two months. The percentages of larvae with conidiation of *M. anisopliae* treated with these three different group conidia, shown in FIG. 7, demonstrate that they were comparable or better than fresh conidia.

TABLE 9

*M. anisopliae* Conidia Viability vs. Gas Composition and Relative Humidity (R.H.) Inside Foil Pouches After Two Months.

| | Gas Composition & Viability After Two Months of Storage | | |
|---|---|---|---|
| Gas Composition at Seal | % $O_2$ | % $CO_2$ | % Viability |
| 25° C. | | | |
| R.H. 0–10% + 20% $O_2$ | 20.9 | 0.0 | 0.0 |
| R.H. 0–10% + 0% $O_2$ | 0.4 | 0.0 | 56.1 |
| R.H. 35–40% + 20% $O_2$ | 20.2 | 0.5 | 20.1 |
| R.H. 35–40% + 0% $O_2$ | 0.4 | 0.0 | 15.2 |
| R.H. 90–100% + 20% $O_2$ | 19.3 | 1.2 | 95.0 |
| R.H. 90–100% + 0% $O_2$ | 0.5 | 0.0 | 37.1 |

TABLE 9-continued

*M. anisopliae* Conidia Viability vs. Gas Composition and Relative Humidity (R.H.) Inside Foil Pouches After Two Months.

| | Gas Composition & Viability After Two Months of Storage | | |
|---|---|---|---|
| Gas Composition at Seal | % $O_2$ | % $CO_2$ | % Viability |
| 37° C. | | | |
| R.H. 0–10% + 20% $O_2$ | 20.5 | 0.0 | 0.0 |
| R.H. 0–10% + 0% $O_2$ | 0.4 | 0.0 | 26.4 |
| R.H. 35–40% + 20% $O_2$ | 20.4 | 0.3 | 0.0 |
| R.H. 35–40% + 0% $O_2$ | 0.4 | 0.0 | 0.0 |
| R.H. 90–100% + 20% $O_2$ | 16.7 | 3.3 | 0.0 |
| R.H. 90–100% + 0% $O_2$ | 0.4 | 0.0 | 0.0 |

In summary, low R.H. packaging provides an environment in which conidia are dehydrated rapidly, and assume dormancy status. The dehydrated conidia stored in a low oxygen environment remain in the stage of dormancy during storage, and therefore they survive well even at an elevated temperature level. However, surface tension is increased by dehydration and germination is reduced after storage. The use of suitable surfactants reduces the surface tension of conidia and facilitates rehydration to break the dormancy.

In this preferred embodiment, the packaging is made of gas-impermeable, water vapor-impermeable, flexible pouch material, such as aluminum foil and low density polyethylene coated aluminum foil. The packaging ensures a consistent oxygen and R.H. levels during storage. Under low oxygen and 0–10% R.H. conditions, conidia of *Beauveria bassiana* survived well at both 25° C. and 37° C. for two months. However, the germination rate of conidia of *Metarhizium anisopliae* stored under the same conditions, low oxygen and 0–10% R.H. at 25° C. and 37° C., are only 56% and 26%, respectively. The soaking of these conidia in a surface active agent, e.g., 0.05% (w/v) ethoxylated tridecyl alcohol, having an HLB of 10 to 15 minutes, significantly increased germination rates to 77% and 74%, respectively.

Modifications and variations of the methods and materials for packaging entomopathogenic fungi will be obvious to those skilled in the art from the foregoing detailed description. Such modifications and variations are intended to come within the scope of the appended claims.

We claim:

1. A method for maintaining the viability of entomopathogenic fungal conidia during storage comprising packaging the conidia in a sealed package wherein the sealed package has an oxygen content of less than 5% and a relative humidity of less than 10%, and the materials forming the package are impermeable to water vapor and other gases, wherein at least 1/200 conidia are viable after two months of storage at a temperature of between 25° C. and 37° C.

2. The method of claim 1 wherein the conidia are packaged with an effective amount of a desiccant and oxygen absorbant to remove humidity and oxygen.

3. The method of claim 1 wherein the oxygen is depleted by using a vacuum or by flushing the package with nitrogen before sealing.

4. The method of claim 1 wherein the conidia are produced by a fungus selected from the group consisting of the genus Metarhizium and the genus Beauveria.

5. Packaged entomopathogenic fungal conidia comprising conidia in a package having an oxygen content of less than 5% and a relative humidity of less than 10%, wherein the materials forming the package are impermeable to water vapor and other gases, wherein at least 1/200 conidia are viable after two months of storage at a temperature of between 25° C. and 37° C.

6. The packaged fungal conidia of claim 5 wherein the conidia are packaged with an effective amount of a desiccant and oxygen absorbant to remove humidity and oxygen.

7. The packaged fungal conidia of claim 5 wherein the fungal conidia are selected from the group consisting of the genus Metarhizium and the genus Beauveria.

8. The packaged fungal conidia of claim 5 wherein the packaging material has (i) an oxygen transmission rate of lower than 0.005 cc of 02/100 sq. inch per day, and (ii) a vapor transmission rate below 0.005 cc of water vapor/100 sq. inch per day.

* * * * *